US011918319B2

(12) United States Patent
Alaie et al.

(10) Patent No.: US 11,918,319 B2
(45) Date of Patent: Mar. 5, 2024

(54) ACOUSTIC TRANSPONDERS FOR WIRELESS PRESSURE MONITORING USING FLEXIBLE ACOUSTIC RESONATORS

(71) Applicant: Cornell University, Ithaca, NY (US)

(72) Inventors: Seyedhamidreza Alaie, New York, NY (US); Amir Ali Amiri Moghadam, New York, NY (US); Subhi Al'Aref, New York, NY (US); James K. Min, Ithaca, NY (US); Bobak Mosadegh, Ithaca, NY (US); Simon Dunham, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 861 days.

(21) Appl. No.: 16/966,408

(22) PCT Filed: Feb. 1, 2019

(86) PCT No.: PCT/US2019/016368
§ 371 (c)(1),
(2) Date: Jul. 30, 2020

(87) PCT Pub. No.: WO2019/152851
PCT Pub. Date: Aug. 8, 2019

(65) Prior Publication Data
US 2020/0359897 A1    Nov. 19, 2020

Related U.S. Application Data

(60) Provisional application No. 62/625,639, filed on Feb. 2, 2018.

(51) Int. Cl.
A61B 5/00    (2006.01)
A61B 5/021   (2006.01)
(Continued)

(52) U.S. Cl.
CPC ........ A61B 5/0028 (2013.01); A61B 5/02141 (2013.01); A61B 5/0215 (2013.01); G01L 11/04 (2013.01); A61B 2562/0247 (2013.01)

(58) Field of Classification Search
CPC . A61B 5/0028; A61B 5/02141; A61B 5/0215; A61B 2562/0247; G01L 11/04
See application file for complete search history.

(56) References Cited

U.S. PATENT DOCUMENTS 6,237,398 B1   5/2001  Porat et al.
6,450,972 B1   9/2002  Knoll
(Continued)

OTHER PUBLICATIONS

International Search Report and Written Opinion in International Patent Application No. PCT/US2019/016368 dated Apr. 29, 2019.
(Continued)

Primary Examiner — Christopher A Flory
(74) Attorney, Agent, or Firm — Foley & Lardner LLP

(57) ABSTRACT

Systems and method to measure pressure are described herein. The system can include a force sensor can that be implanted into a patient to measure, for example, cardiac pressure. The force sensor can include first and second film layers that can define a plurality of pressure cells. An external pressure can deform the pressure cells and change their resonant frequency. When exposed to an acoustic signal, the pressure cells can resonant at a pressure-dependent resonant frequency. The system can detect reflected acoustic waves generated by the resonance of the pressure cells. The system can convert the frequency readings into pressure values.

25 Claims, 9 Drawing Sheets

(51) Int. Cl.
*A61B 5/0215* (2006.01)
*G01L 11/04* (2006.01)

(56) References Cited

U.S. PATENT DOCUMENTS

| | | |
|---|---|---|
| 6,770,032 B2 | 8/2004 | Kaplan |
| 2004/0211260 A1 | 10/2004 | Girmonsky et al. |
| 2006/0117859 A1* | 6/2006 | Liu .................... A61B 5/02152 73/753 |
| 2007/0107522 A1 | 5/2007 | Oikawa et al. |
| 2016/0302729 A1 | 10/2016 | Starr et al. |

OTHER PUBLICATIONS

International Preliminary Report on Patentability PCT PCT/US2019/016368, dated Aug. 13, 2020.

* cited by examiner

ACOUSTIC TRANSPONDERS FOR
WIRELESS PRESSURE MONITORING
USING FLEXIBLE ACOUSTIC RESONATORS

CROSS-REFERENCE TO RELATED
APPLICATION

The present application is a U.S. National Stage Application under 35 U.S.C. § 371 of International Application No. PCT/US2019/016368, filed Feb. 1, 2019, which claims the benefit of, and priority to, U.S. Provisional Patent Application 62/625,639, filed Feb. 2, 2018, the entire disclosures of which are incorporated herein by reference for all purposes.

BACKGROUND OF THE DISCLOSURE

The measurement of internal pressures can provide information for the diagnosis and treatment of medical conditions. For example, blood pressure can provide insight into the functioning and health of a patient's heart. In some instances, a physician may desire to know pressure values from directly within the heart.

SUMMARY OF THE DISCLOSURE

The present disclosure describes a miniaturized force sensor that can include acoustic resonators. The acoustic resonators can resonate at different frequencies, when exposed to an acoustic wave, based on the force applied to the acoustic resonators. The resonators can be passive and, in some implementations, do not include internal electronics or batteries. The external force can cause the acoustic resonators to deform, which can alter the acoustic resonator's resonant frequency. The force sensors are biocompatible to provide in-vivo force monitoring. For example, the force sensor can be implanted into cardiac tissue of a patient to provide cardiac and vascular pressure monitoring.

According to at least one aspect of the disclosure, a method to measure forces can include applying a first acoustic wave to a force sensor. The force sensor can be deployed in a region. The force sensor can include at least one film layer define a plurality of pressure cells that change resonant frequencies responsive to changes in external force in the region. The method can include determining a frequency of a second acoustic wave generated in response to the first acoustic wave. The second acoustic wave can be generated by a resonance of the plurality of pressure cells based on an external force in the region. The method can include determining a force value of the external force based on the frequency of the second acoustic wave.

In some implementations, determining the frequency of the second acoustic wave generated in response to the first acoustic wave can include determining a frequency shift between the first acoustic wave and the second acoustic wave. The method can include deploying the force sensor across a septum of a heart through a catheter. The force sensor can include a first film layer and a second film layer.

The method can include anchoring the force sensor to a wall of the heart atrium. The first film layer can include a plurality of ridges that can be coupled with the second film layer to define the plurality of pressure cells. The method can include generating the first acoustic wave with an ultrasound transducer. The method can include receiving the second acoustic wave generated in response to the first acoustic wave with the ultrasound transducer.

The method can include generating the first acoustic wave with a frequency between 5 MHz and 10 MHz. Each of the plurality of pressure cells can have a diameter between 10 µm and 1 mm. The method can include determining the frequency of the second acoustic wave further comprising detecting a frequency shift between −20 kHz and 140 kHz.

According to at least one aspect of the disclosure, a force sensor can include a first film layer. The force sensor can include at least one film layer to define a plurality of pressure cells between the first film layer and the second film layer. The plurality of pressure cells can generate a second acoustic wave responsive to a first acoustic wave that is incident on the plurality of pressure cells. The second acoustic wave can have a frequency based on a resonance of the plurality of pressure cells that varies based on an amount of external force to which the force sensor is exposed.

In some implementations, the first film layer can include a plurality of ridges and at least portion of the second film layer is coupled with the plurality of ridges to form the plurality of pressure cells between the first film layer and the second film layer. The force sensor can include a polymer encapsulating the first film layer and the second film layer. The first film layer and the second film layer can include an elastomeric material. The plurality of pressure cells can each define a volume that can include at least one of a liquid and an inert gas. A first subset of the plurality of pressure cells can each include a reference liquid, and a second subset of the plurality of pressure cells each comprise a reference gas.

The force sensor can include a structural support disposed toward the perimeter of the first film layer and the second film layer. The structural support can deploy the first film layer and the second film layer to a substantially planar configuration. In some implementations, the structural support can anchor the force sensor to tissue.

The force sensor can include a third film layer that can include a second plurality of ridges. The force sensor can include a fourth film layer coupled with the second plurality of ridges to define a second plurality of pressure cells between the third film layer and the fourth film layer. The second plurality of pressure cells can deform responsive to a second external force to change a second resonant frequency of the second plurality of pressure cells. The force sensor can include a support structure coupling the first film layer and the second film layer with the third film layer and the fourth film layer. Each of the plurality of pressure cells have a diameter between 10 µm and 1 mm.

According to at least one aspect of the disclosure, a kit can include a force sensor. The force sensor can at least one film layer to define a plurality of pressure cells between the first film layer and the second film layer. The plurality of pressure cells can generate a second acoustic wave responsive to a first acoustic wave incident on the plurality of pressure cells. The second acoustic wave can have a frequency based on a resonance of the plurality of pressure cells that varies based on an amount of external force to which the force sensor is exposed. The kit can include a catheter to deploy the force sensor.

In some implementations, each of the plurality of pressure cells have a diameter between 10 µm and 1 mm.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes force sensors that can include acoustic resonators. The force sensors can be used to measure pressures, such as a gas, fluid, or other form of pressure exerted on the force sensor. The resonant frequency of the acoustic resonators can be pressure dependent such that the acoustic resonators resonate at different frequencies when exposed to different pressures. The acoustic resonators can include a plurality of pressure cells defined between two thin films. The pressure cells can be filled with liquids, voids (e.g., contain a vacuum), gases, solids, or a combination thereof. The contents of the pressure cells can be compliant at different pressures. The change in resonant frequency can be detected by exposing the force sensor to acoustic waves (e.g., ultrasound waves). The force sensor can reflect the ultrasound waves at the force sensor's resonant frequency.

Figure 1:
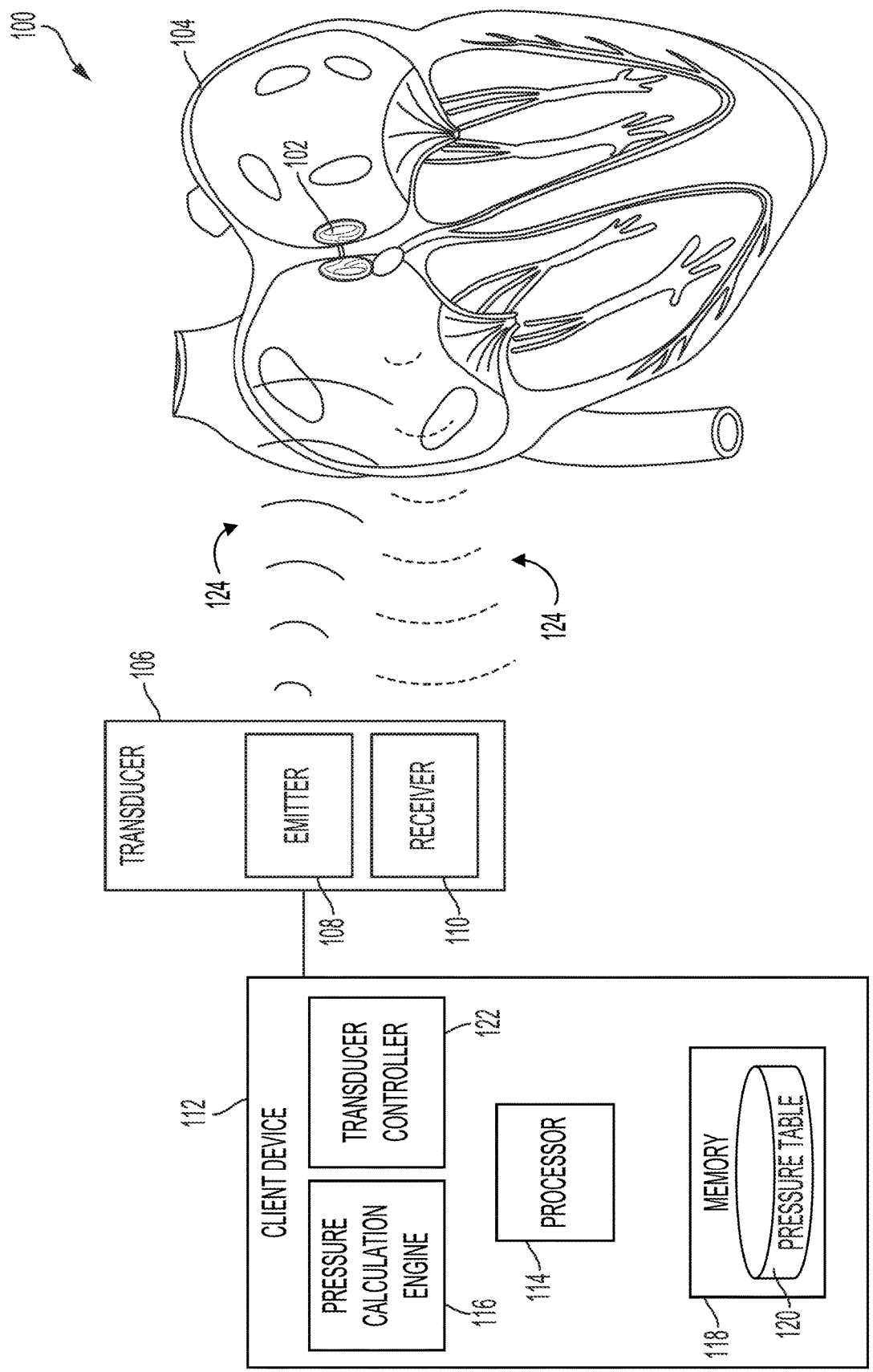
FIG. 1 illustrates an example system to measure pressure.

FIG. 1 illustrates an example system 100 to measure pressure. The system 100 can include one or more force sensors 102. The force sensors 102 can be implanted, deployed, or attached to biological tissue, such as the heart 104. The force sensors 102 can be deployed to non-biological targets, such as within pressure vessels. The force sensors 102 can interface with transducers 106 through acoustic waves 124. For example, the transducers 106 can include emitters 108 to generate acoustic waves 124 and receivers 110 to receive acoustic waves 124 reflected from the force sensor 102. The transducer 106 can be controlled by client devices 112. The client devices 112 can include one or more processors 114 to execute the functions described herein. The client device 112 can include one or more pressure calculation engines 116 and transducer controllers 122. The client devices 112 can include memory 118 that can include one or more pressure tables 120.

The system 100 can include one or more force sensors 102. The force sensors 102 are described in further detail in relation to FIGS. 2-9. The force sensor 102 can be a passive device. The force sensor 102 can be passive by not including electronics, such as batteries or energy conversion units. For example, the force sensor 102 can be passive by not including an energy conversion unit that can convert the ultrasound signals into electrical energy that the force sensor 102 uses in the transmission of data from the force sensor 102 to an external receiver. The force sensor 102 can be passive by reflecting or backscattering ultrasound signals (e.g., acoustic waves 124) to an external receiver with a frequency that indicates a pressure exerted on the force sensor 102. The force sensor 102 can reflect or backscatter the acoustic waves at a resonant frequency that is proportional to a pressure applied to the force sensor 102.

The force sensor 102 can include a plurality of pressure cells. The pressure cells can be pressurized cells and are further described in relation to FIGS. 2-7, among others. The pressure cells can include volumes defined between two thin films. One or more of the thin films can deflect, deform, or otherwise stretch into or away from the volume based on the pressure external to the pressure cells and force sensor 102. The deflection of the thin films can change the resonant frequency of the pressure cells. The pressure cells can act as resonators when exposed to acoustic waves 124. The resonant frequencies of the pressure cells can change based on a pressure applied to the pressure cells. For example, different external pressures can cause a thin film across the pressure cells to deform—changing the resonant frequency of the pressure cells and the force sensor 102. The client device 112 can determine the force sensor's resonant frequency (under a given external pressure) based on the acoustic waves 124 reflected back to the transducer 106 from the force sensor 102. For example, the client device 112 can calculate a frequency shift of the reflected acoustic waves and calculate a pressure value based on the detected frequency shift. The frequency shift can be a frequency shift between the output acoustic waves 124 and the reflected acoustic waves 124. The frequency shift can be a frequency shift between the reflected acoustic waves 124 during a measurement phase and the reflected acoustic waves 124 during a calibration phase (or when the force sensor 102 is exposed to a known pressure (e.g., 1 ATM)). The frequency shift can be determined by determining an amplitude peak in an Fast Fourier Transform (FFT) of the output acoustic waves 124. The amplitude peak can occur at the frequency of the output acoustic waves 124 in the FFT. The shifted frequency can be determined by determining an amplitude peak in an FFT of the reflected acoustic waves 124. The shift can be the difference between frequencies indicated by the peaks identified in the two FFTs.

The system 100 can include one or more client devices 112. The client device 112 can control the transducer 106 and can analyze the reflected acoustic waves 124 to determine the pressure applied to the force sensor 102. The client device 112 can include any type and form of computing device. The client device 112 can include or be a component of an ultrasound system, a desktop computer, laptop computer, portable computer, tablet computer, wearable computer, embedded computer, or any other type and form of computing device. The client device 112 can include a processor 114 and memory 118. The client device 112 can include or otherwise execute a pressure calculation engine 116 and a client device 112.

The client device 112 can include processors 114 and memory 118. The memory 118 can store machine instructions that, when executed by the processor 114, cause the processor 114 to perform one or more of the operations described herein. The processor 114 can include a microprocessor, ASIC, FPGA, etc., or combinations thereof. The processor 114 can be a multi-core processor or an array of processors. The memory 118 can include, but is not limited to, electronic, optical, magnetic, or any other storage devices capable of providing the processor 114 with program instructions. The memory 118 can include a floppy disk, CD-ROM, DVD, magnetic disk, memory chip, ROM, RAM, EEPROM, EPROM, flash memory, optical media, or any other suitable memory from which the processor 114 can read instructions. The instructions can include code from any suitable computer programming language, such as, but not limited to, C, C++, C #, Java, JavaScript, Perl, HTML, XML, Python, and Visual Basic.

The client device 112 can store one or more pressure tables 120 in the memory 118. The pressure table 120 can be a data structure that the pressure calculation engine 116 uses in converting data (e.g., frequency data) received from the reflecting acoustic waves 124 into pressure values. The pressure table 120 can include a lookup table containing frequency-pressure pairs. For example, the pressure calculation engine 116 can use a frequency value as a looking key for input into the lookup table. Inputting the lookup key (e.g., frequency) into the lookup table can return a pressure value. In some implementations, the pressure table 120 can include one or more functions for calculating a pressure value as a function of frequency.

The client device 112 can include one or more pressure calculations engines 116. The pressure calculation engine 116 can be an application, applet, script, service, daemon, routine, or other executable logic to calculate pressure values based on input frequencies. The pressure calculation engine 116 can receive data from the transducer 106 and calculate pressure values based on the received data. For example, the transducer 106 can transmit to the pressure calculation engine 116 a signal that includes an indication of the received, reflected acoustic waves 124. The pressure calculation engine 116 can determine the frequency content of the signal by, for example, calculating a FFT of the signal. The pressure calculation engine 116 can identify a primary peak in the frequency content. In some implementations, the pressure calculation engine 116 can determine the frequency of the acoustic waves 124 transmitted from the emitter 108 and can determine a frequency shift between the transmitted acoustic waves 124 and the received acoustic waves 124. For example, when setting the output frequency of the emitter 108, the transducer controller 122 can set in the memory 118 the current output frequency. The pressure calculation engine 116 can read the output frequency from the memory 118 to determine the initial frequency. The pressure calculation engine 116 can determine the difference between the initial frequency and the frequency determined for the primary peak in the signal including the reflected acoustic waves 124. The frequency shift can be between about −20 kHz and about 200 kHz, between about 0 kHz and about 150 kHz, or between about 5 kHz and about 100 kHz.

The pressure calculation engine 116 can use the frequency of the primary peak (or the value of the frequency shift) to determine a pressure value of an external pressure applied to the force sensor 102. For example, the pressure calculation engine 116 can use the frequency as a lookup key for determining the pressure value from the pressure table 120. If the frequency, when used as a key to lookup pressure values in the pressure table 120 is an intermediate value and does not correspond to a frequency value stored in the pressure table 120, the pressure calculation engine 116 can interpolate a pressure value for the frequency based on the neighboring pressure values that are stored in the pressure table 120. For example, the frequency can be rounded down to a step value contained in the pressure table 120 and up to a step value contained in the pressure table 120 to identify the input frequency's neighboring values. The pressure calculation engine 116 can use the frequency as an input to a function to calculate pressure values based on an input frequency. The function can be a piecewise function or continuous over a range of input frequencies.

The client device 112 can include one or more transducer controllers 122. The transducer controller 122 can be an application, applet, script, service, daemon, routine, or other executable logic to control the transducer 106. The transducer controller 122 can send instructions to the transducer 106 to set the output frequency of the acoustic waves 124 generated by the emitter 108. The transducer controller 122 can set the emitter 108 to generate acoustic waves 124 at a constant frequency over the course of a measurement session. The transducer controller 122 can set the emitter 108 to generate acoustic waves 124 at varying frequencies. For example, the transducer controller 122 can set a start frequency, an end frequency, a step size, and a duration for the emitter 108. The emitter 108 can sweep between the start frequency and the end frequency (and back), stepping between frequencies at the instructed step size. The emitter 108 can transmit the acoustic waves 124 at each step frequency for the duration set by the transducer controller 122. The transducer controller 122 can set an output frequency for the emitter 108 to between about 2 MHz and about 15 MHz, between about 5 MHz and about 12 MHz, between about 5 MHz and about 10 MHz, or between about 7 MHz and about 10 MHz.

The system 100 can include a transducer 106. The transducer 106 can be an ultrasound transducer. The transducer 106 can generate and transmit acoustic waves 124 via the emitter 108 and receive reflected acoustic waves 124 via the receiver 110. In some implementations, the emitter 108 and the receiver 110 can be separate devices. The emitter 108 can generate and emit acoustic waves 124. For example, the emitter 108 can include a piezoelectric ceramic (or other material) that deforms when pulsed with an electric signal. The piezoelectric ceramic can be pulsed to generate acoustic waves 124 at a predetermined frequency. The acoustic waves 124 can be ultrasound waves. The emitter 108 can generate acoustic waves 124 with a frequency between about 2 MHz and about 15 MHz. The emitter 108 can generate acoustic waves 124 with relatively small wavelengths (e.g., less than a mm) in liquids and solids. The receiver 110 can acoustic waves 124 that are reflected back to the transducer 106 by the force sensor 102. The receiver 110 can convert the reflected acoustic waves 124 into a signal. The signal can be an analog signal or a digital signal. The receiver 110 can amplify the signal. The receiver 110 can transmit the signal to the client device 112 and pressure calculation engine 116. In some implementations, the transducer 106 (or the client device 112) can store the signal from the receiver 110 to the memory 118 for later or off line analysis.

Figure 2B:
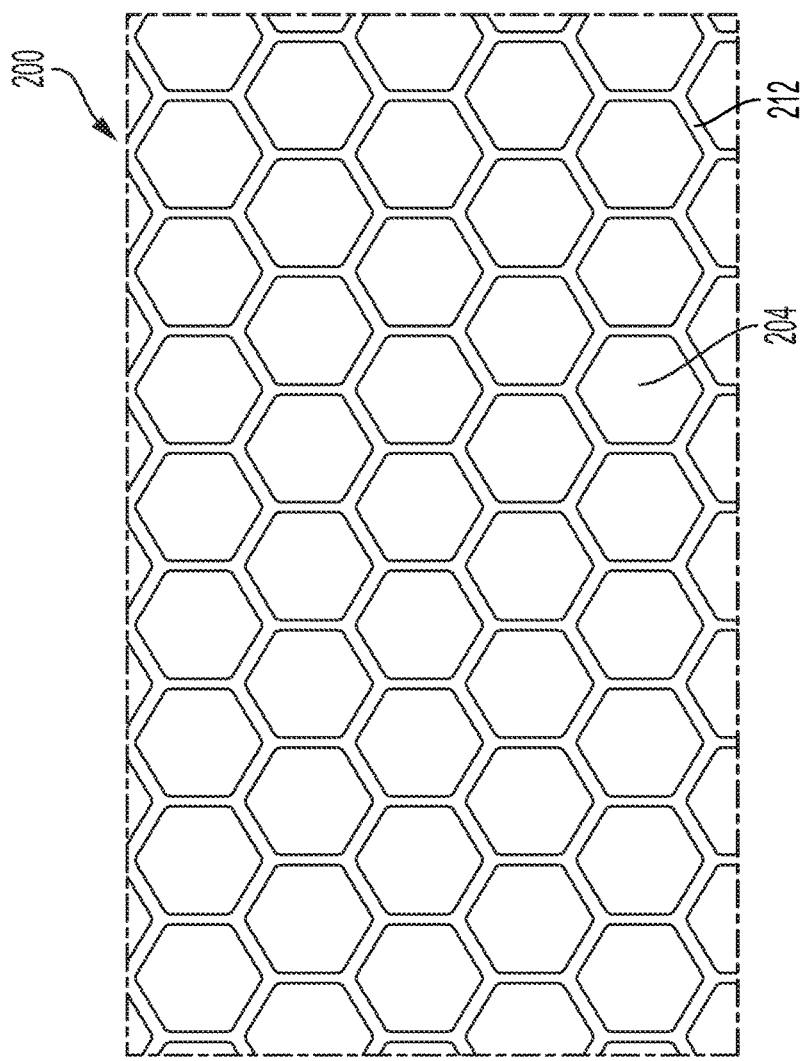
FIG. 2. illustrates an example force sensor that can be used in the example system illustrated in FIG. 1.
Figure 2A:
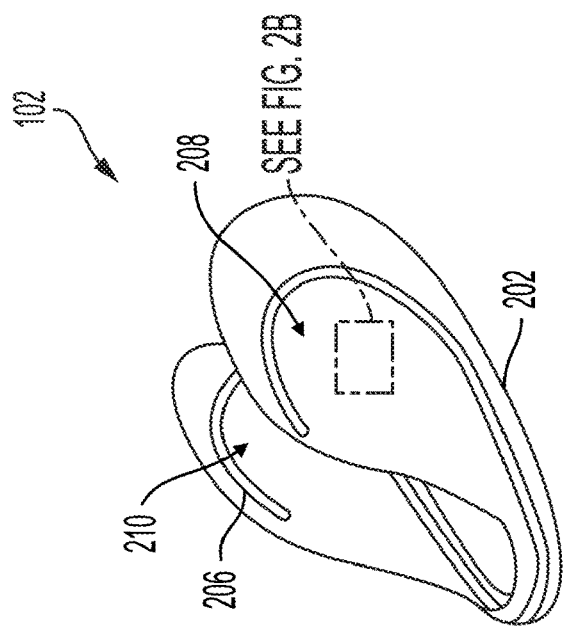

FIG. 2A illustrates an example force sensor 102 that can be used in the example system illustrated in FIG. 1. FIG. 2B illustrates an enlarged view 200 of the pressure cells 204. The force sensor 102 can include one or more film layers 202 that can include or define the pressure cells 204. The film layers 202 can be coupled with a support structure 206 to provide structural support to the one or more film layers 202.

The force sensor 102 can include a support structure 206. The support structure 206 can include a biocompatible metal, plastic, or other material. The support structure 206 can have a shape memory such that the support structure 206 can be compressed or rolled to fit within a delivery catheter and then return to an original shape (e.g., planner shape) when deployed from the catheter. In some implementations, the force sensor 102 can deploy to a non-planar shape. For example, the force sensor 102 can deploy to a shape that contours to a surface of the target tissue to which the force sensor 102 is anchored. The support structure 206 can include a shape memory alloy (e.g., nitinol), metal alloy (e.g., stainless steel), metal (e.g., titanium), plastic, or other biocompatible material. The support structure 206 can include one or more loops that can provide structural support to one or more force sensors 102. For example, as illustrated in FIG. 2A, the support structure 206 can form a first acoustic resonator 208 and a second acoustic resonator 210. The first acoustic resonator 208 and the second acoustic resonator 210 are illustrated as loops, but can include any geometrical shape. The first acoustic resonator 208 and the second acoustic resonator 210 function as separate force sensors to provide separate pressure values. For example, the film layers 202 within each of the first acoustic resonator 208 and the second acoustic resonator 210 can be configured differently (e.g., have differently sized pressure cells 204). In some implementations, the first acoustic resonator 208 and the second acoustic resonator 210 can be disposed within different anatomical locations. For example, and as illustrated in FIG. 1, a first acoustic resonator can be disposed within a first atrium of the heart and a second acoustic resonator can be disposed within the second atrium of the heart to provide pressure readings from both the left and right atrium. The support structure 206 can be disposed toward a perimeter of the film layers 202 within each of the first acoustic resonator 208 and the second acoustic resonator 210. The support structure 206 can be laminated between the film layers 202 or coupled with an outer surface of one of the film layers 202. The force sensor 102 can include between about 1 and about 10, between about 1 and about 8, between about 1 and about 6, between about 1 and about 4, or between about 1 and about 2 acoustic resonators.

Each of the first acoustic resonator 208 and the second acoustic resonator 210 can have a height between about 10 µm and about 1 mm, between about 100 µm and about 1 mm, between about 200 µm and about 900 µm, between about 300 µm and about 800 µm, between about 300 µm and about 700 µm, or between about 300 µm and about 600 µm.

FIG. 2B illustrates an enlarged view 200 of the pressure cells 204 within each of the acoustic resonators 208 and 210. The film layer 202 can define or include a plurality of pressure cells 204. For example, one or more of the film layers 202 can include a plurality of ridges 212. The ridges 212 of a first film layer 202 can be coupled with a surface of a second film layer 202 to define the plurality of pressure cells 204. In some implementations, the pressure cells 204 can be microbubbles that are sealed between two film layers 202. The first film layer 202 and the second film layer 202 can be different portions of the same film layer 202. For example, a portion of the film layer 202 can include the plurality of ridges 212. A second portion of the film layer 202 can be folded over and coupled with the ridges 212 or first portion of the film layer 202 to form the plurality of pressure cells 204.

The ridges 212 can have a height between about 10 µm and about 1 mm, between about 100 µm and about 1 mm, between about 200 µm and about 900 µm, between about 300 µm and about 800 µm, between about 300 µm and about 700 µm, or between about 300 µm and about 600 µm. The ridges 212 can have a width between about 1 µm and about 200 µm, between about 10 µm and about 200 µm, between about 10 µm and about 150 µm, or between about 50 µm and about 150 µm. The pressure cells 204 can have a diameter (or width) between about 10 µm and about 1000 µm, between about 200 µm and about 800 µm, between about 200 µm and about 600 µm, or between about 200 µm and about 400 µm. In some implementations, the pressure cells 204 can have a diameter of about 300 µm. Each of the pressure cells 204 can have a diameter of substantially the same size or different groups of the pressure cells 204 can be configured differently. For example, the height or diameter of the pressure cells 204, the fluid (or lack thereof) within the volume defined by the pressure cells 204, or the thickness of the ridges 212 can vary at different locations of the film layers 202. In some implementations, the diameter or other parameter (e.g., height and ridge thickness) can be based on the wavelength of the acoustic waves 124 generated by the emitter 108.

Figure 3:
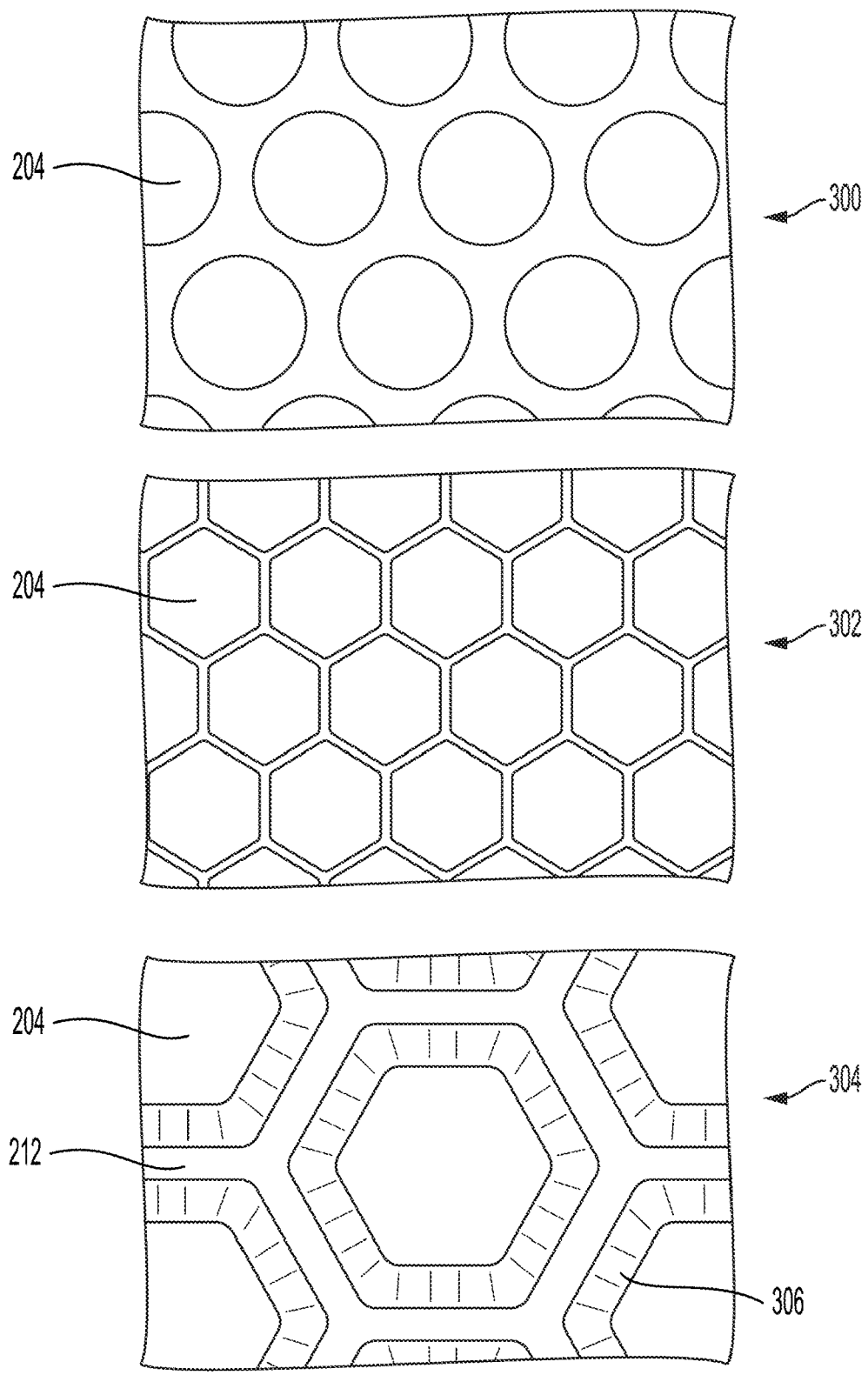
FIG. 3 illustrates a plurality of example pressure cells that can be used in the force sensor illustrated in FIG. 2.

FIG. 3 illustrates a plurality of example pressure cells that can be used in the force sensors described herein. The pressure cells 204 can have a plurality of cross-sectional shapes. The pressure cells 204 can have circular, triangular, square, rectangular, pentagonal, hexagonal, or other cross-sectional shape. The enlarged view 300 illustrates pressure cells 204 with a circular configuration. In some implementations, holes or pores can be defined in, for example, a layer of polydimethylsiloxane (PDMS). The layer can be coupled between two film layers 202 to define the pressure cells 204. The enlarged view 302 illustrates pressure cells 204 with a honeycomb or hexagonal configuration. The thickness of the ridges 212 can be substantially uniform along their height to form pressure cells 204 with substantially uniform diameters along their height. In some implementations, the thickness of the ridges 212 can vary along their height. Varying the thickness of the ridges along their height can form pressure cells 204 that taper. For example, as illustrates in the enlarged view 304, the pressure cells 204 can include tapered regions 306. The tapered region 306 can provide a smooth transition between the walls of the ridges 212 and the face of the film layer 202.

Figure 4:
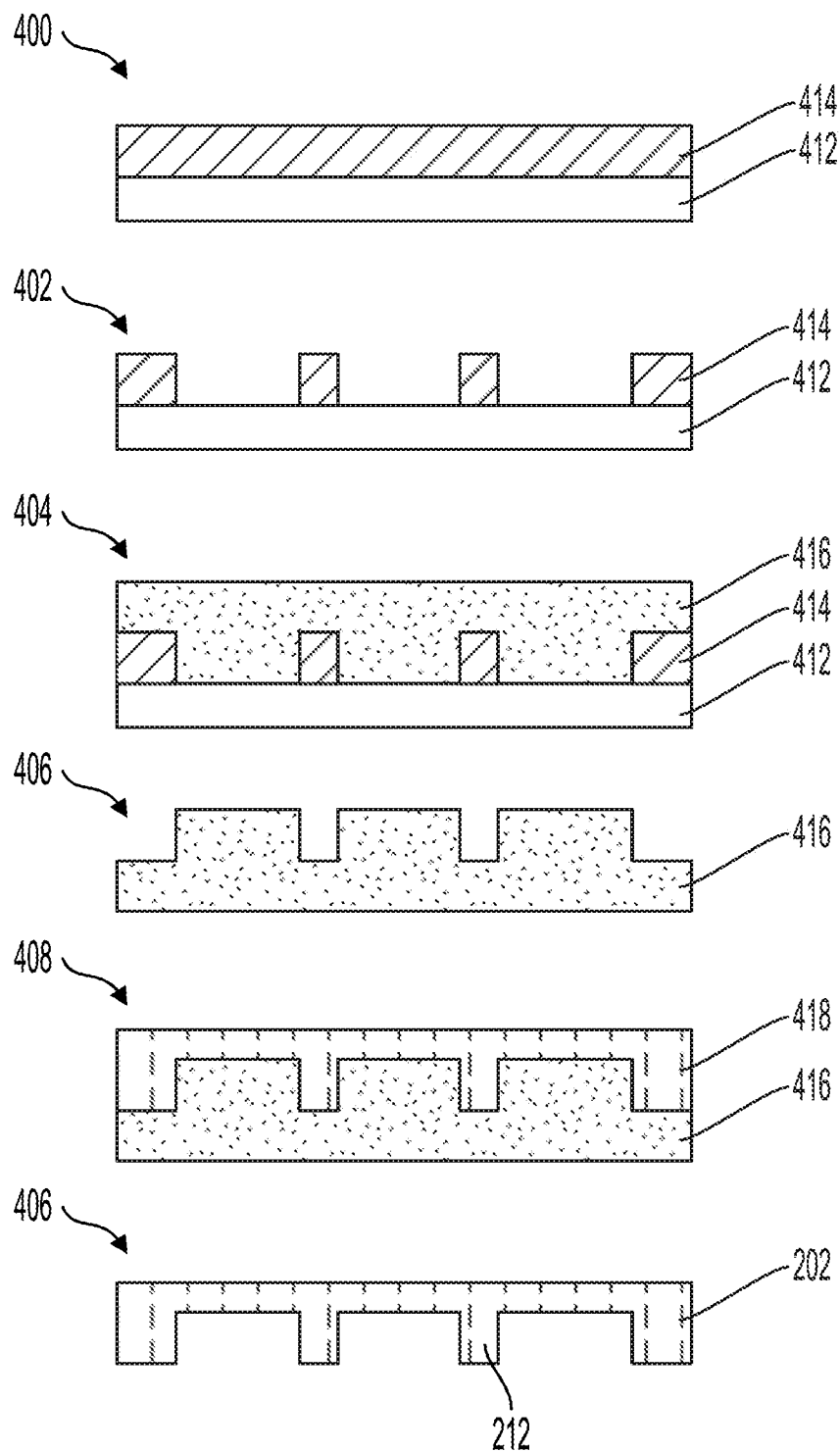
FIGS. 4 and 5 illustrate a method to manufacture the example force sensor illustrated in FIG. 2.
Figure 5:
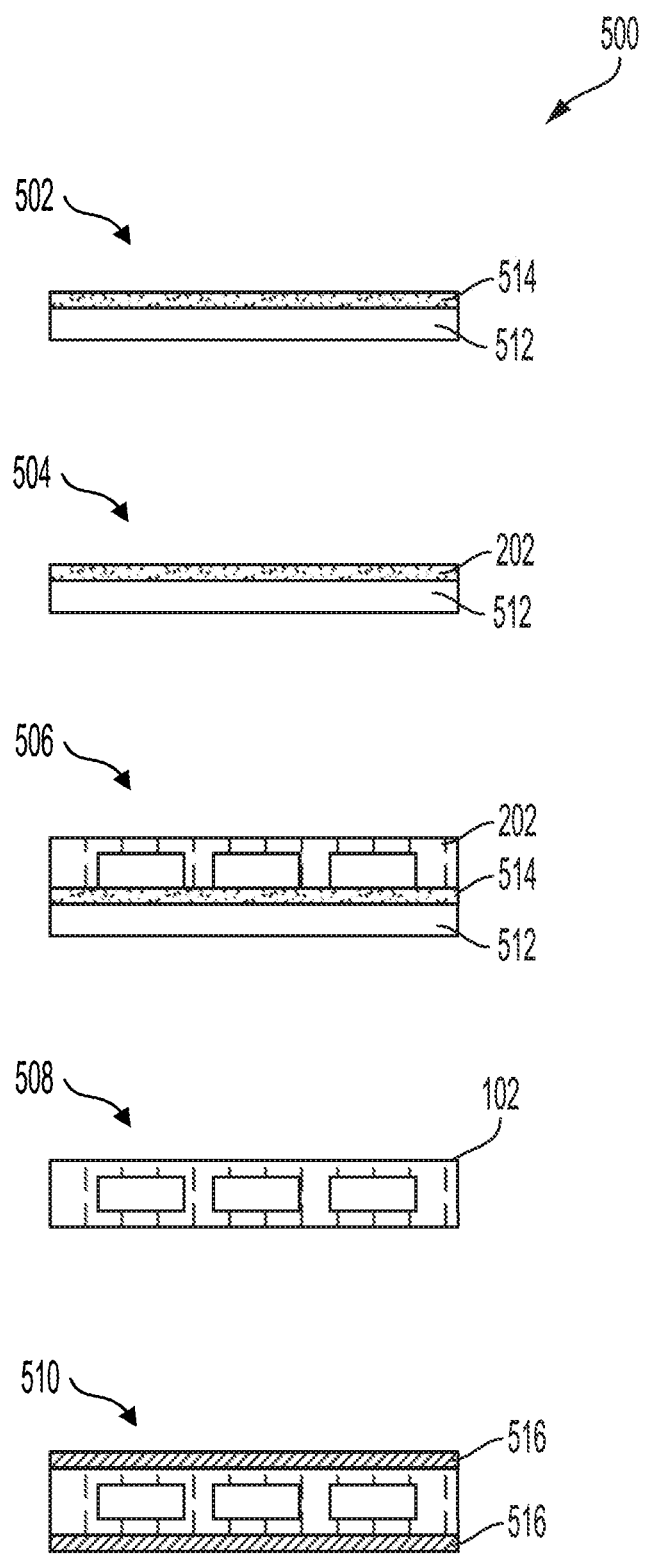

FIGS. 4 and 5 illustrate a method to manufacture the example force sensor. At step 400 a photoresist 414 can be applied to a silicon wafer 412. The photoresist 414 can be an epoxy-based photoresist, such as SU-8. The photoresist 414 can be applied to the silicon wafer 412 through a spin coating process, deposition process, or spreading process. The photoresist 414 can be applied to a thickness of between about 100 µm and about 1000 µm, between about 100 µm and about 800 µm, between about 200 µm and about 600 µm, or between about 200 µm and about 400 µm. At step 402, a portion of the photoresist 414 can be cured. For example, portions of the photoresist 414 can be covered with a mask. The exposed portions of the photoresist 414 (e.g., the portions not covered by the mask) can be cured. The photoresist 414 can be cured with ultraviolet (UV) light, heat, or other curing methods. The curing process can cause the cured portions of the photoresist 414 to become cross-linked and harden. As illustrated at step 402, the uncured portions of the photoresist 414 (and the mask) can be removed or washed from the silicon wafer 412. In some implementations, all of the photoresist 414 can be cured and the photoresist 414 can be machined or etched to pattern the photoresist 414.

At step 404, an encapsulant 416 can be applied to the patterned photoresist 414. The encapsulant 416 can be applied to the patterned photoresist 414 by spin coating the encapsulant 416 onto the photoresist 414. The encapsulant 416 can be applied by spreading or deposition. The encapsulant 416 can be cured. The encapsulant 416 can be cured with UV light, heat, or the addition of a curing agent. At step 406, the cured encapsulant 416 can be removed from the photoresist 414 and silicon wafer 412 to form a mold for forming one of the film layers of the force sensor. At step 408, a polymer 418 an be applied to encapsulant 416. The polymer 418 can be spin coated, spread, or deposited onto the encapsulant 416. The polymer 418 can include a thermoset polymer, thermoplastic polymer, biocompatiable polymers, or other polymers. In some implementations, the polymer 418 can be PDMS. The polymer 418 can be cured to set the polymer 418. The polymer 418 can be cured with UV light, heat, or a curing agent. When cured, at step 406, the cured polymer 418 can be removed from the encapsulant 416 to form a first film layer 202. The film layer 202 can include a plurality of ridges 212. In some implementations, the ridges 212 can be formed into a layer of cured PDMS by etching or micro-machining out volumes to define the ridges 212.

FIG. 5 illustrates a method 500 to manufacture a second film layer. At step 502, a polymer 514 can be applied to a silicon wafer 512. The polymer 514 can be applied to the wafer 512 by spin coating, deposition, or spreading. The polymer 514 can be of the same composition as the polymer 418. For example, both the polymer 514 and polymer 418 can include an elastomeric material, such as PDMS, Polymer Polyglycolic-Lactic Acid (PGLA), Polyglycolide (PGA), polylactic acid (PLA), or a combination thereof. In some implementations, the polymer 514 and the polymer 418 can be different polymers or different materials. In some implementations, the second film layer 202 can include or can be a metal film layer. The metal film layer can include titanium.

After applied to the silicon wafer, the polymer 514 can be cured. At step 504, the polymer 514 can be cured to form a second film layer 202. The polymer 514 can be cured by exposure to UV light, heat, or a curing agent. At step 506, the first film layer 202 (generated at step 406) can be deposited onto the cured polymer 514. The first film layer 202 can be bonded to the second film layer 202 with a bonding agent. The bonding agent can include a UV curable silicone, uncured sylgard 184 resin, $O_2$ plasma based bonding, heat, stamping, or any combination thereof. At step 508, the first film layer 202 and the second film layer 202 can be removed from the silicon wafer 512 to form the force sensor 102. At step 510, either face of the force sensor 102 can be encapsulated in a thin film 516. The thin film 516 can include polyurethane or a fabric.

Figure 6:
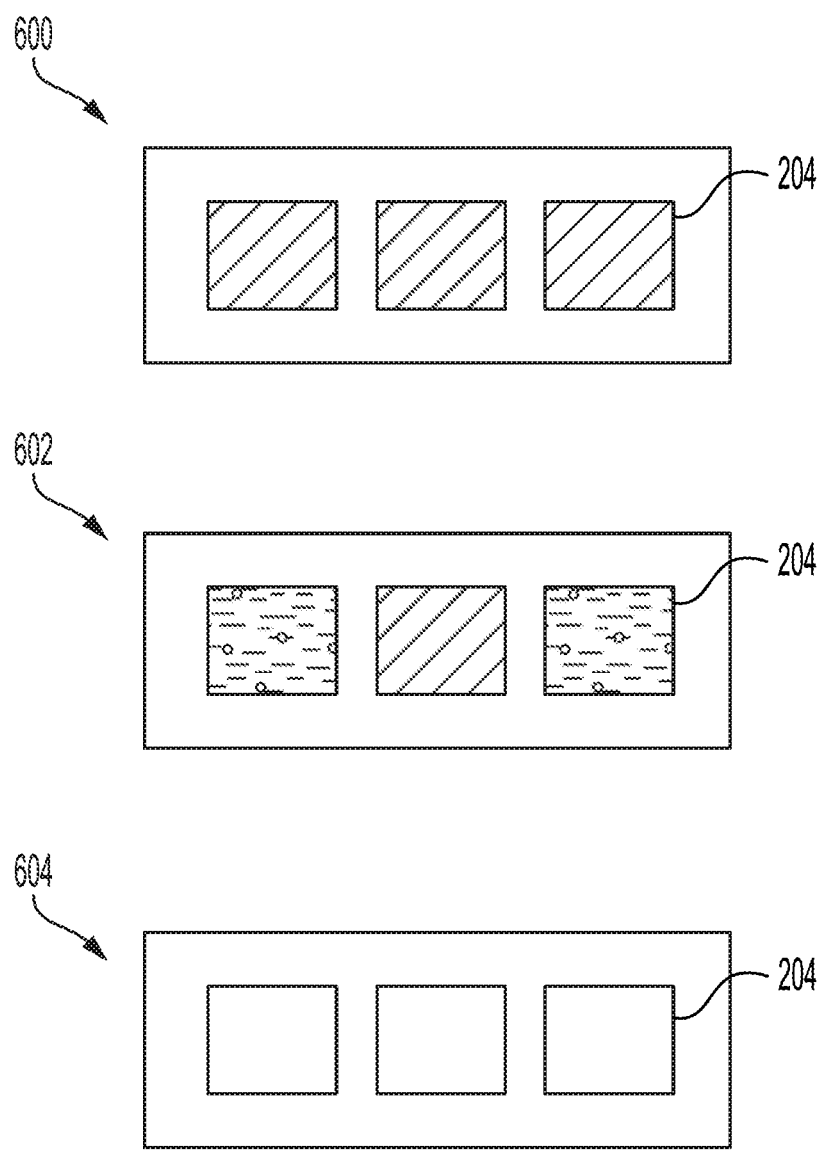
FIG. 6 illustrates cross-sectional views of example pressure cells that can be used in the force sensor illustrated in FIG. 2.

FIG. 6 illustrates cross-sectional views of example pressure cells that can be used in the force sensor. The volumes defined by the pressure cells can be filled with a fluid or can include a vacuum (e.g., substantially not include a fluid). The fluid can be a gas or a liquid. The gas can include air, oxygen, carbon dioxide, nitric oxide, or any combination thereof. The liquid can include water, saline, glycerin, oil (e.g., silicone oil and coconut oil), and any combination thereof. The fluid can be acoustically active with respect to blood. For example, the fluid can have a bulk modulus or density that is different from the force sensor's external environment (e.g., blood when the force sensor 102 is positioned within a heart atrium). The acoustically active fluid can create a boundary condition that can reflect or scatter acoustic waves 124 applied to the force sensor 102.

Each of the pressure cells can include the same fluid. A first portion of the pressure cell can include a first fluid and a second portion of the pressure cell can include a second fluid. For example, as illustrated by configuration 600, the pressure cells 204 of the force sensor can each be filled with the same fluid. As illustrated in configuration 602, neighboring pressure cells 204 can contain different fluids. The force sensors 102 can be configured in an alternating, ABAB, configuration where neighboring pressure cells 204 alternate between two fluids. In some implementations, each of the pressure cells 204 within a given row of the force sensor 102 can include a first fluid and each of the pressure cells 204 in neighboring rows of the force sensor 102 can include a second fluid. In some implementations, the pressure cells 204 can be configured in a checkerboard configuration such that each of a pressure cell's neighbor pressure cells contain a different fluid than the pressure cell. As illustrated in the configuration 604, one or more of the pressure cells 204 can include a vacuum. For example, the pressure cells 204 can be substantially devoid of a fluid.

Figure 7:
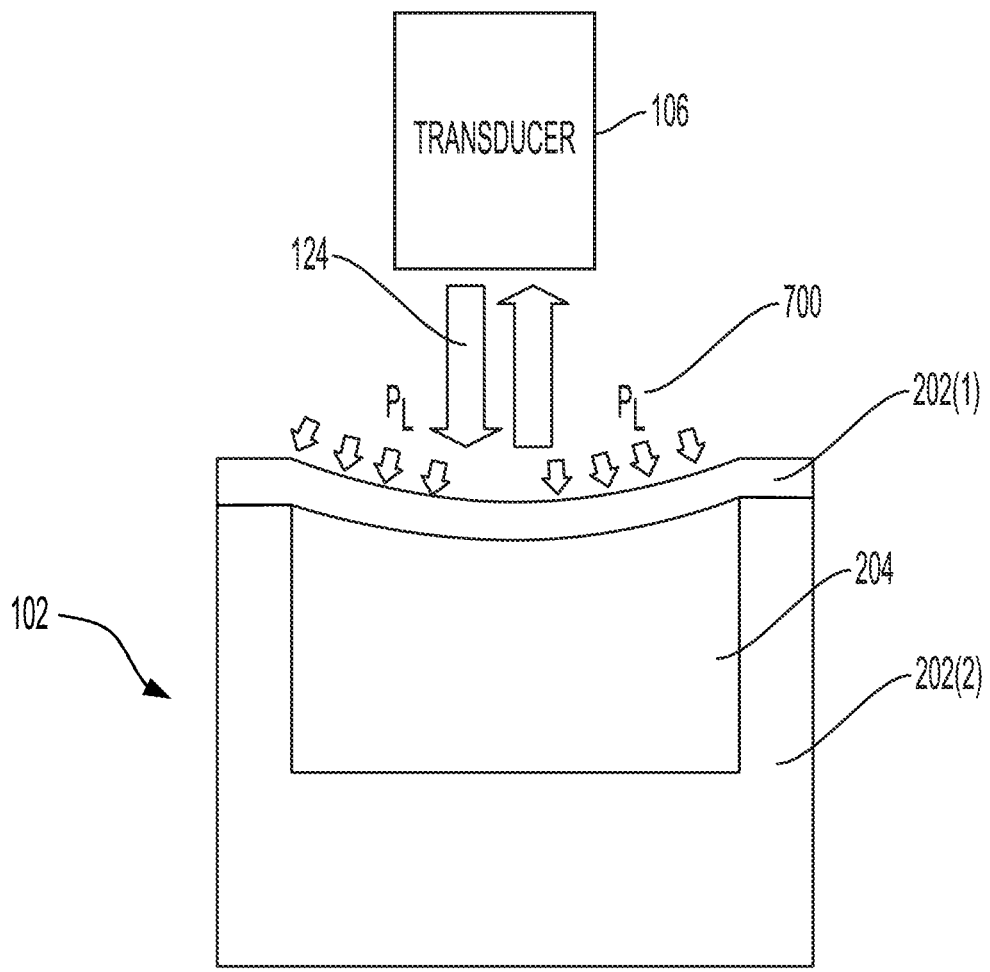
FIG. 7 illustrates a block diagram illustrating the operation of an example pressure cell that can be a pressure cell in the example force sensor illustrated in FIG. 2.

FIG. 7 illustrates a block diagram illustrating the operation of an example pressure cell 204 from a force sensor 102. The force sensor 102 can include a plurality of pressure cells 204 that are defined between a first film layer 202(1) and a second film layer 202(2). The external pressure 700 can deform the film layer 202(1) inward, toward the pressure cell 204. In some implementations, under low external pressure (e.g., when the external pressure 700 is less than the internal pressure of the pressure cell 204), the film layer 202(1) can deform outward, away from the pressure cell 204. The deformation of the film layer 202(1) can stretch the film layer 202(1). The deformation of the film layer 202(1) can change the frequency at which the film layer 202(1) resonates when the force sensor 102 is exposed to acoustic waves 124 from the transducer 106. The film layers 202(1) can resonate to provide a detectable backscattered of the acoustic waves 124 (e.g., an ultrasound signal) based on the principle of Fabry Perot-type cavity, etalon-type cavity, brag scattering, Mie resonance, and any other type of mechanical resonance.

Figure 8:
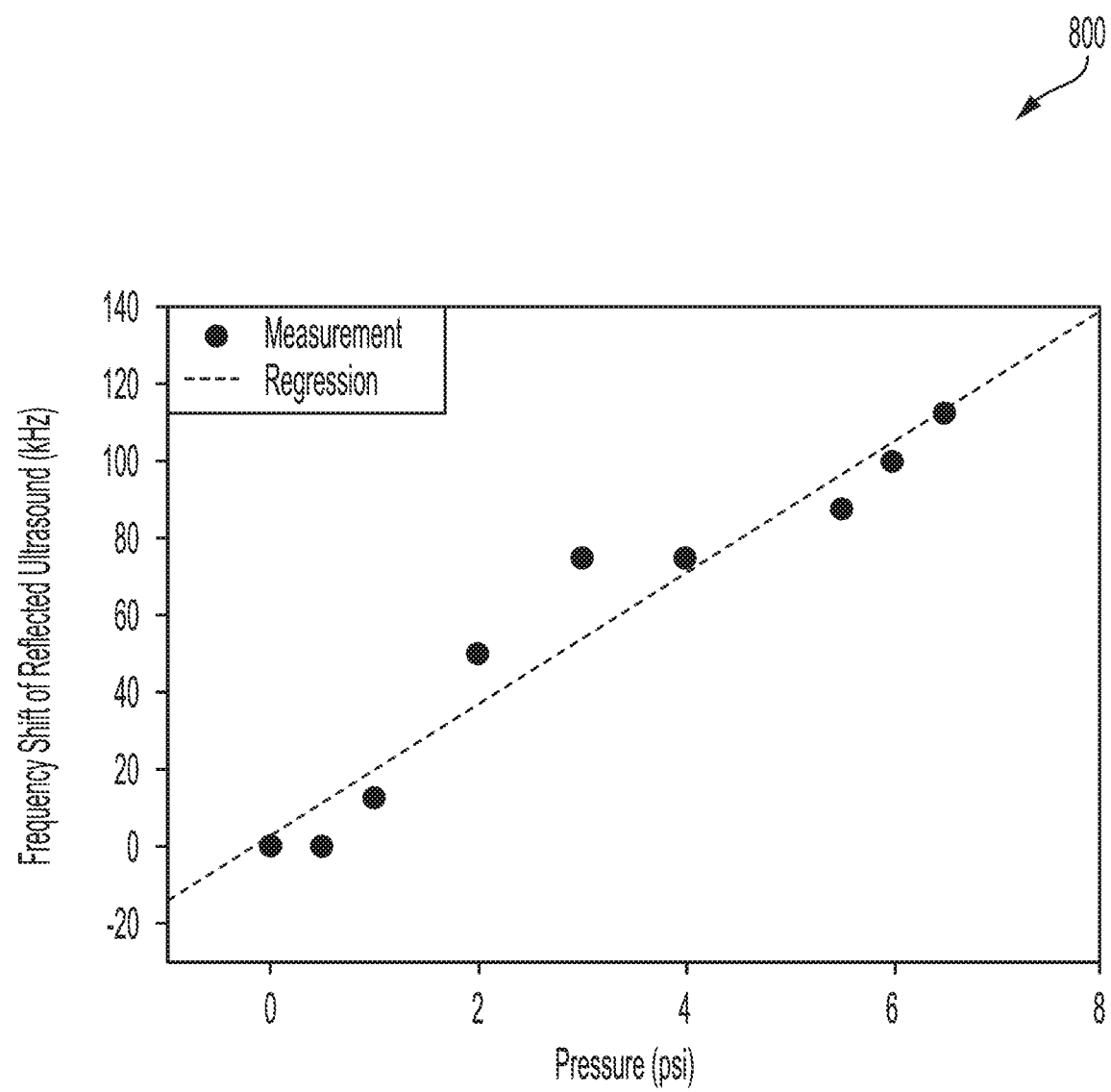
FIG. 8 illustrates a graph of an example force sensor's response to an acoustic wave.

FIG. 8 illustrates a graph 800 of an example force sensor's response to an acoustic signal. To generate the data illustrated in the graph 800, a force sensor as described herein was inserted into a pressure vessel filled with water. The pressure vessel was pressurized to predetermined pressure levels to exert an external pressure force on the force sensor. A ultrasound signal was applied to the force sensor. The transducer's receiver detected the backscatter or reflected acoustic waves. The client device detected the resonant peaks of the reflected acoustic waves and determined a frequency shift between the transmitted acoustic waves and the received acoustic waves. The graph 800 illustrates that the applied pressure and the value of the frequency shift have a high level or correlation and provide for a linear relationship between the pressure and detected frequency shift.

Figure 9:
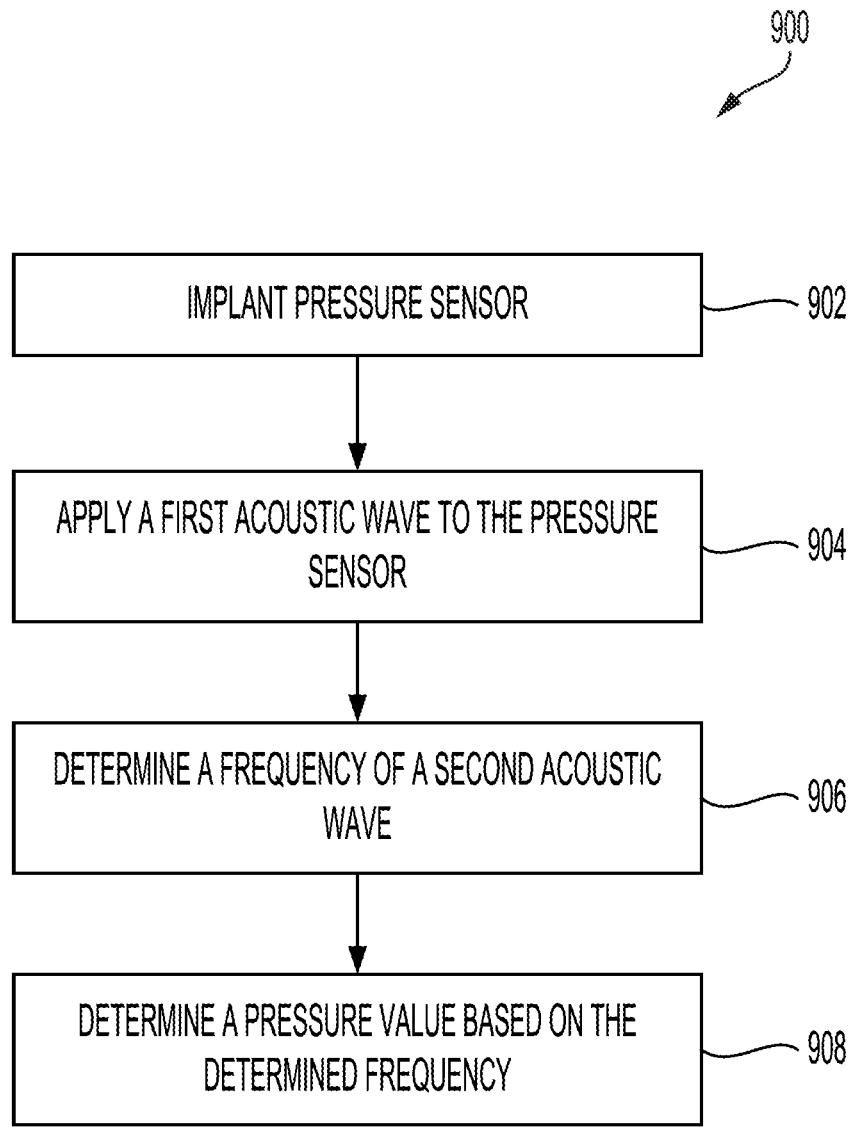
FIG. 9 illustrates a block diagram of an example method to measure pressure with the force sensor illustrated in FIG. 2.

FIG. 9 illustrates a block diagram of an example method to measure pressure. The method 900 can include implanting the force sensor (BLOCK 902). The method 900 can include applying a first acoustic wave to the force sensor (BLOCK 904). The method 900 can include determining a frequency of a second acoustic wave (BLOCK 906). The method 900 can include determining a pressure value based on the determined frequency (BLOCK 908).

As set forth above, the method 900 can include implanting a force sensor (BLOCK 902). Also referring to FIGS. 1 and 2, among others, the force sensor 102 can include a plurality of film layers 202 that can define a plurality of pressure cells 204. The force sensors 102 can be implanted or deployed to a region. The force sensor 102 can be used for medical purposes, and the force sensor 102 can be deployed to an internal organ. For example, the force sensor 102 can be deployed to an atrium or ventricle of the heart, other portion of a patient's vasculature, stomach, intestine, bladder, abdominal cavity, pelvic cavity, thoracic cavity, spinal cavity, or cranial cavity. The force sensor 102 can deployed to an external surface, such as on a patient's skin. The force sensor 102 can be deployed through a catheter. For example, the force sensor 102 can be deployed to the patient's heart through transcatheter implantation. Also referring to FIG. 1, the force sensor 102 can be deployed across a septum of the patient's heart. For example, a first portion of the force sensor 102 can be deployed into the right atrium and a second portion of the force sensor 102 can be deployed in the left atrium of the patient's heart. The portion of the force sensor 102 crossing the septum can anchor the force sensor 102 to the patient's heart. In some implementations, the pressure table 120 can include an anchoring device, such as a hook or adhesive to anchor the force sensor 102 to a patient's tissue. The force sensor 102 can be sutured to the patient's tissue to anchor the force sensor 102 to the patient.

In some implementations, the force sensor 102 can be used for non-medical pressure monitoring. For example, the force sensor 102 can be used to measure pressures with pipes or tubing.

The method 900 can include applying a first acoustic wave (BLOCK 904). The transducer controller 122 can set a frequency for the first acoustic wave. The transducer's emitter 108 can generate the first acoustic wave at the frequency set by the transducer controller 122. For example, the emitter 108 can generate the first acoustic wave at a frequency between 2 MHz and about 15 MHz, between about 5 MHz and about 12 MHz, between about 5 MHz and about 10 MHz, or between about 7 MHz and about 10 MHz. For example, if the force sensor 102 is implanted into an atrium of a patient's heart, the transducer 106, as part of an ultrasound probe, can be applied to the patient's chest to emit acoustic waves towards the patient's heart and the force sensor 102. Ultrasound or other gel can be applied to the transducer 106 or patient's chest to reduce attenuation of the acoustic signals at the patient-transducer interface.

The method 900 can include determining a frequency of a second acoustic wave (BLOCK 906). With reference to FIG. 1, among others, the second acoustic waves can be the acoustic waves 124 that are reflected back to the transducer 106 in response to the acoustic waves 124 transmitted from the transducer 106 toward the force sensor 102. The pressure cells can resonant at a predetermined frequency in response to an external pressure. The resonance generated in response to the acoustic waves can be due to changes in many, individual pressure cells whose individual resonance has been changed in response to the external pressure, due to the behavior of many pressure cells that provide a coupled response that is characteristic of the frequency shift, or a combination thereof. The second acoustic waves can be transmitted or reflected back to the transducer 106 at the pressure cells' resonant frequency. For example, the external pressure can deflect or stretch a film layer of the pressure cells. The deflection of the film layer can cause the resonance of the pressure cells to change. When exposed to the first set of acoustic waves from the transducer 106, the pressure cells (or one or more of the film layers thereof) can resonant. The resonance of the pressure cells can generate reflected acoustic waves that are detected by the transducer 106. The pressure calculation engine 116 can determine the frequency of the second acoustic waves. For example, the pressure calculation engine 116 can calculate an FFT of the signal generated by the receiver 110 containing indications of the second acoustic waves. The pressure calculation engine 116 can identify the frequency of the second acoustic waves as a peak in the FFT signal. In some implementations, the pressure calculation engine 116 can determine a frequency shift between the acoustic waves 124 output by the emitter 108 and the acoustic waves 124 received by the receiver 110. In some implementations, in addition to or in place of, the pressure calculation engine 116 can determine an amplitude shift of the acoustic waves 124. The pressure calculation engine 116 can base the pressure calculation on the amplitude shift of the acoustic wave 124. For example, when exposed to 1 ATM the acoustic waves 124 can have a first amplitude and when exposed to the 1.5 ATM the acoustic waves 124 can have a second amplitude that is greater than or less than the first amplitude.

The method 900 can include determining a pressure value based on the determined frequency (BLOCK 908). Also referring to FIG. 1, among others, the client device 112 can include a pressure table 120. The pressure table 120 can be a lookup table that includes a plurality of pressure values that are indexed to frequency values. The client device 112 can use the determined frequency from BLOCK 906 as a key to select a value from the lookup table. In some implementations, the client device 112 can include one or more functions for the calculation of pressure values based on an input frequency. The client device 112 can calculate or select a pressure value based on the determined frequency and can display the pressure value to a user of the client device 112. The client device 112 can store the pressure value to the memory 118 for later retrieval or display.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to, plus, or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only "A", only "B", as well as both "A" and "B". Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A method comprising:
    applying a first acoustic wave to a force sensor deployed in a region, the force sensor comprising (i) at least one film layer defining a plurality of pressure cells that change resonant frequencies responsive to changes in external pressure in the region, and (ii) a structural support that is shapable to orient a first pressure cell of the plurality of pressure cells relative to a second pressure cell of the plurality of pressure cells;
    determining a frequency of a second acoustic wave generated in response to the first acoustic wave, the second acoustic wave generated by a resonance of the plurality of pressure cells based on an external force in the region; and
    determining a force value of the external force based on the frequency of the second acoustic wave.

2. The method of claim 1, wherein determining the frequency of the second acoustic wave generated in response to the first acoustic wave further comprises determining a frequency shift between the first acoustic wave and the second acoustic wave.

3. The method of claim 1, further comprising deploying the force sensor across a septum of a heart through a catheter.

4. The method of claim 1, further comprising anchoring the force sensor to a wall of the heart atrium.

5. The method of claim 1, wherein the at least one film layer comprises a first film layer and a second film layer defining the plurality of pressure cells.

6. The method of claim 5, wherein the first film layer comprises a plurality of ridges coupled with the second film layer to define the plurality of pressure cells.

7. The method of claim 1, further comprising:
    generating the first acoustic wave with an ultrasound transducer; and
    receiving the second acoustic wave generated in response to the first acoustic wave with the ultrasound transducer.

8. The method of claim 1, further comprising generating the first acoustic wave with a frequency between 5 MHz and 10 MHz.

9. The method of claim 1, wherein each the plurality of pressure cells has a diameter between 10 µm and 1 mm.

10. The method of claim 1, wherein determining the frequency of the second acoustic wave further comprises detecting a frequency shift between −20 kHz and 140 kHz.

11. The method of claim 1, further comprising deploying the force sensor across a septum of a heart such that at least a first pressure cell of the plurality of cells is positioned on a first side of the septum and at least a second pressure cell of the plurality of cells is positioned on a second side of the septum.

12. A force sensor, comprising:
    at least one film layer to define a plurality of pressure cells, the plurality of pressure cells configured to generate a second acoustic wave responsive to a first acoustic wave incident on the plurality of pressure cells, the second acoustic wave having a frequency based on a resonance of the plurality of pressure cells that varies based on an amount of external force to which the force sensor is exposed; and
    a structural support that is shapable to orient a first pressure cell of the plurality of pressure cells relative to a second pressure cell of the plurality of pressure cells.

13. The force sensor of claim 12, wherein the at least one film layer comprises a first film layer coupled with at least a portion of a second film layer.

14. The force sensor of claim 13, wherein the first film layer comprises a plurality of ridges and at least portion of the second film layer is coupled with the plurality of ridges to form the plurality of pressure cells between the first film layer and the second film layer.

15. The force sensor of claim 12, further comprising a polymer encapsulating the at least one film layer.

16. The force sensor of claim 12, wherein the at least one film layer comprises an elastomeric material.

17. The force sensor of claim 12, wherein the plurality of pressure cells each defines a volume comprising at least one of a liquid and an inert gas.

18. The force sensor of claim 12, wherein the structural support is disposed toward the perimeter of a first film layer and a second film layer, and wherein the structural support deploys the first film layer and the second film layer to a substantially planar configuration.

19. The force sensor of claim 18, wherein the structural support is configured to anchor the force sensor to tissue.

20. The force sensor of claim 12, further comprising:
a third film layer comprising a second plurality of ridges; and
a fourth film layer coupled with the second plurality of ridges to define a second plurality of pressure cells between the third film layer and the fourth film layer, the second plurality of pressure cells configured to deform responsive to a second external force to change a second resonant frequency of the second plurality of pressure cells;
wherein the structural support couples the at least one film layer with the third film layer and the fourth film layer.

21. The force sensor of claim 12, wherein each of the plurality of pressure cells has a diameter between 10 μm and 1 mm.

22. The force sensor of claim 12, wherein the structural support has shape memory such that the structural support tends toward a shape following deviation of the structural support from the shape.

23. A force sensor comprising:
at least one film layer to define a plurality of pressure cells, the plurality of pressure cells configured to generate a second acoustic wave responsive to a first acoustic wave incident on the plurality of pressure cells, the second acoustic wave having a frequency based on a resonance of the plurality of pressure cells that varies based on an amount of external force to which the force sensor is exposed;
wherein a first subset of the plurality of pressure cells each comprises a reference liquid and a second subset of the plurality of pressure cells each comprises a reference gas.

24. A kit comprising:
a force sensor, comprising (i) at least one film layer to define a plurality of pressure cells, the plurality of pressure cells configured to generate a second acoustic wave responsive to a first acoustic wave incident on the plurality of pressure cells, the second acoustic wave having a frequency based on a resonance of the plurality of pressure cells that varies based on an amount of external force to which the force sensor is exposed, and (ii) a structural support that is shapable to orient a first pressure cell of the plurality of pressure cells relative to a second pressure cell of the plurality of pressure cells; and
a catheter to deploy the force sensor.

25. The kit of claim 24, wherein each of the plurality of pressure cells has a diameter between 10 μm and 1 mm.

* * * * *